United States Patent [19]

Schenk et al.

[11] 4,092,347

[45] May 30, 1978

[54] 1-CHLORO-PROP-2-ENE-3-SULFONIC ACID COMPOUNDS AND THEIR MANUFACTURE

[75] Inventors: Walter Schenk, Bad Durkheim; Helmut Schlecht, Ludwigshafen; Guenther Gotsmann, Frankenthal, all of Germany

[73] Assignee: BASF Aktiengesellschaft, Ludwigshafen, Germany

[21] Appl. No.: 725,846

[22] Filed: Sep. 23, 1976

[30] Foreign Application Priority Data

Oct. 11, 1975 Germany .......................... 2545660

[51] Int. Cl.$^2$ ...................... C07C 143/16; C07F 3/06; C07F 3/10; C25D 3/12
[52] U.S. Cl. ............................ 260/513 R; 260/429.9; 260/431; 260/439 R; 260/513 H; 204/49
[58] Field of Search ................ 260/513 R, 429.9, 431, 260/439 R

[56] References Cited

U.S. PATENT DOCUMENTS

| | | | |
|---|---|---|---|
| 3,048,625 | 8/1962 | Distler et al. | 260/513 R |
| 3,730,854 | 5/1973 | Schenk et al. | 260/513 R |
| 3,969,399 | 7/1976 | Passal | 260/513 R |

*Primary Examiner*—Nicky Chan
*Attorney, Agent, or Firm*—Keil, Thompson & Shurtleff

[57] ABSTRACT

The new 1-monochloro- and 1,1-dichloro-prop-2,3-ene-3-sulfonic acids and their metal salts, and a process for their manufacture by reacting chloropropanesulfonic acid compounds with alkali metal carbonates, alkali metal bicarbonates and/or alkaline earth metal hydroxides at from 5° to 100° C to give 1-chloro-prop-2,3-ene-3-sulfonates which may then be reacted with acid compounds in a second step.

The products are starting materials for the manufacture of pesticides, plasticizers, solvents, leather greases, detergents, lubricating oils, synthetic resins and slip agents. They are also assistants in electroplating processes and starting materials for the manufacture of such assistants.

4 Claims, No Drawings

1-CHLORO-PROP-2-ENE-3-SULFONIC ACID COMPOUNDS AND THEIR MANUFACTURE

The present invention relates to new compounds which are 1-monochloro- and 1,1-dichloro-prop-2-ene-3-sulfonic acids and their metal salts, and to a process for their manufacture by reacting chloropropanesulfonic acid compounds with alkali metal carbonates, alkali metal bicarbonates and/or alkaline earth metal hydroxides at from 5° to 100° C to give 1-chloro-prop-2-ene-3-sulfonates, which may be reacted with acid compounds in a second step.

Ullmanns Encyklopadie der technischen Chemie, volume 16, page 571, discloses that 1-chlorobutane-4-sulfonic acid is formed by hydrolysis of 1-chlorobutane-4-sulfonic acid chloride. The manufacture of 1-chloro-prop-2-ene-3-sulfonic acid has not hitherto been disclosed.

It is an object of the present invention to provide a new process whereby the new 1-chloro-prop-2,3-ene-3-sulfonic acid compounds may be manufactured simply and economically, starting from readily accessible starting materials, in good yield and high purity.

It is a further object of the present invention to provide the new 1-mono- and 1,1-dichloro-prop-2,3-ene-3-sulfonic acids and their metal salts.

We have found that the latter object is achieved by providing the new 1-chloro-prop-2-ene-3-sulfonic acid compounds of the formula

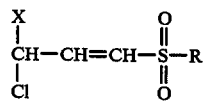

where X is hydrogen or chlorine, R is hydroxyl or —OY and Y is one equivalent of a metal atom.

Further, we have found that the first-mentioned object is achieved and that 1-chloro-prop-2-ene-3-sulfonic acid compounds of the formula

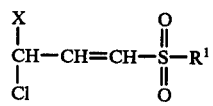

where X is hydrogen or chlorine, $R^1$ is hydroxyl or —OZ and Z is an alkali metal atom or one equivalent of an alkaline earth metal atom are obtained advantageously by a method wherein chloropropanesulfonic acid compounds of the formula

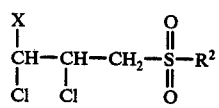

where X is hydrogen or chlorine, $R^2$ is hydroxyl, chlorine or —OZ and Z is an alkali metal atom or one equivalent of an alkaline earth metal atom, are reacted with alkali metal carbonates, alkali metal bicarbonates and/or alkaline earth metal hydroxides at from 5° to 100° C to give 1-chloro-prop-2,3-ene-3-sulfonates of the formula

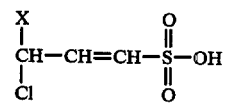

where X and Z have the above meanings and, in an optional second step, the compounds III are reacted with acid compounds to give 1-chloro-prop-2,3-ene-3-sulfonic acids of the formula

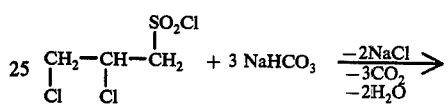

where X has the above meanings.

When 1,2-dichloropropane-3-sulfonic acid chloride, sodium bicarbonate and hydrochloric acid are used, the reaction can be represented by the following equations:

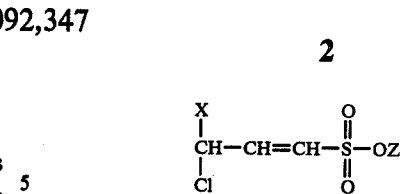

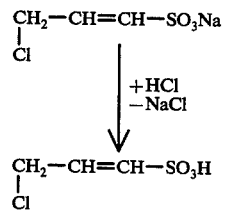

The process of the invention gives the new 1-chloro-prop-2,3-ene-3-sulfonic acid compounds simply and economically, starting from easily accessible starting materials, in good yield and high purity. It was surprising that both in the reaction with the bases and in the production of the acid, the compound III and compound IV, respectively, are obtained in high yield and that the formation of by-products, e.g. alkali metal salts or alkaline earth metal salts of the chloropropanesulfonic acid starting materials, salts of monohydroxy- and dihydroxy-monochloropropane-sulfonic acids, salts of dihydroxy- and trihydroxy-propanesulfonic acids, condensation products with one or more chlorine and/or hydroxyl groups, sulfones or polymerization products of the above compounds are substantially avoided. The chloropropanesulfonic acid starting compound can be manufactured by reacting 1,2-dichloropropane with sulfur dioxide and chlorine to give 1-chloropropanesulfonic acid chlorides, if appropriate followed by a second step of hydrolysis of the chlorides with water at elevated temperature to give chloropropanesulfonic acids; this economical utilization of 1,2-dichloropropane, formed as a by-product of the synthesis of propylene oxide by the chlorohydrin process, is of substantial industrial interest.

Suitable starting materials are 1,2-dichloro-propane-3-sulfochloride, 1,1,2-trichloro-propane-3-sulfochloride and the corresponding two sulfonic acids. They may be reacted with the above bases in stoichiometric amount or in excess, preferably, in the case of the manufacture of the 1-monochloro-prop-2,3-ene-3-sulfonic acid compound I or of the 1,1-dichloro-prop-2,3-ene-3-sulfonic acid compound I, in a ratio, respectively, of from 3 to 3.5 equivalents of base per mole of 1,2-dichloropropane-sulfonic acid chloride II and of from 2 to 2.5 equivalents of base per mole of 1,2-dichloropropanesulfonic acid II or its alkali metal sulfonate or alkaline earth metal sulfonate II. The reaction is carried out at from 5° to 100° C, preferably from 10° to 90° C, under atmospheric or superatmospheric pressure, batchwise or, preferably, continuously. The base used is an alkali metal bicarbonate, preferably potassium bicarbonate and especially sodium bicarbonate, or an alkali metal carbonate, preferably potassium carbonate and especially sodium carbonate, or an alkaline earth metal hydroxide, preferably magnesium hydroxide, barium hydroxide and especially calcium hydroxide, or a mixture of any two or more of such compounds. Barium hydroxide and calcium hydroxide are preferred for the manufacture of end products IV which are to be free from alkali metal chloride. As a rule, the starting material II is reacted in the presence of water, advantageously in an amount of from 150 to 250 per cent by weight, based on starting material II, a convenient method being to use from 50 to 30 per cent strength by weight aqueous solutions or suspensions of the bases.

The reaction may be carried out as follows: a mixture of starting material II, base and, advantageously, water is kept at the reaction temperature for from 0.5 to 2 hours. The end product is then isolated from the reaction mixture by conventional methods, e.g. by evaporating the solution and recrystallizing the residue from a suitable solvent, e.g. ethanol or dimethylformamide. In general, however, it is advantageous to carry out the reaction continuously. Where alkaline earth metal hydroxides are used as bases, preferred reaction temperatures are from 20° to 40° C initially, e.g. during the first half of the reaction time, and from 65° to 100° C finally, e.g. during the second half of the reaction time, whilst in the case of alkali metal carbonates and alkali metal bicarbonates the corresponding figures are an initial temperature of from 5° to 15° C and a final temperature of from 60° to 75° C. Mixtures of bases may also be used; in a preferred embodiment, the reaction is carried out with sodium bicarbonate, preferably at a pH of from 7 to 8, and sodium carbonate is then added and the pH brought to 9.5; this method gives an end product of improved stability to light and heat during storage. To manufacture the 1,1-dichloro-prop-2,3-ene-3-sulfonic acid compounds, the reaction conditions described above are as a rule observed.

Instead of employing the starting material II, the reaction mixtures obtained from its manufacture may also be used; in an operationally and economically advantageous method the reaction mixture from the manufacture of chloropropanesulfonic acid chloride can advantageously be used for the reaction. This mixture from the reaction of 1,2-dichloropropane with sulfur dioxide and chlorine essentially contains, in addition to the starting sulfochloride II, unconverted 1,2-dichloropropane and minor amounts of more highly chlorinated propanes, e.g. 1,1,2-, 1,2,2- and 1,2,3-trichloropropane, 1,2,2,3-tetrachloropropane, 1,1,2,2-tetrachloropropane and 1,1,1,2,2-pentachloropropane. These chlorohydrocarbon mixtures act as solvents and diluents for the reaction according to the invention and subsequently, by helping to form the organic phase of the reaction mixture, facilitate the isolation of the end product III contained in the aqueous phase.

Reaction of the above 1-monochloro-prop-2,3-ene-sulfonate III and 1,1-dichloro-prop-2,3-ene-sulfonate III with acid compounds in stoichiometric amount or in excess, preferably in an amount of from 1 to 1.1 equivalents of acid compounds per mole of compound III, gives 1-monochloro-prop-2,3-ene-sulfonic acid and 1,1-dichloro-prop-2,3-ene-sulfonic acid, respectively. The reaction is in general carried out at from 15° to 50° C, preferably from 15° to 25° C, under atmospheric or superatmospheric pressure, continuously or batch-wise. Inorganic or organic acids having a pK of less than 1.5 may be used as the acid compounds. Instead of monobasic acids, equivalent amounts of polybasic acids may be used. Examples of suitable acids are hydrogen chloride, hydrogen bromide, hydrogen iodide, perchloric acid, sulfuric acid, phosphoric acid, nitric acid and acid ion exchangers. The acids can be used in a concentrated form, as a mixture with one another and/or as a mixture with a solvent, especially water. It is preferred to carry out the reaction in an aqueous medium, advantageously in the presence of from 15 to 25 moles of water per mole of starting material III.

Particularly preferred acid compounds are mineral acids, e.g. hydrochloric acid or sulfuric acid, advantageously in the form of aqueous solutions of from 10 to 35 percent strength by weight.

The reaction can be carried out as follows: a mixture of starting material III and water is passed continuously, at the reaction temperature, over a column reactor filled with the exchanger. Alternatively, the above mixture, together with the exchanger or with one of the above acids, can be treated batchwise by keeping it at the reaction temperature for from 120 to 150 minutes. The end product is isolated in the conventional manner, e.g. by evaporation, from the continuously discharged mixture, or from the mixture obtained from the batchwise reaction.

The corresponding metal salts can be produced from the free acid, advantageously in the form of its aqueous solution, by reaction with metal compounds, e.g. with metal hydroxides, metal oxides or metal salts, such as chlorides or nitrates. Advantageously, the reaction mixture from the manufacture of the free acid is used directly, the metal compound is added and the mixture is advantageously brought to a ratio of from 15 to 35 moles of water per mole of end product IV. Preferred metal salts of the end products IV are those of metals of groups Ia, IIa, IIb and VIIIb of the periodic table (D'Ans-Lax, Taschenbuch fur Chemiker und Physiker (Springer, Berlin, 1967), volume I, page 63), especially the nickel, cobalt, cadmium, zinc, mercury, sodium, potassium or magnesium salt.

The new compounds I or Ia which can be manufactured by the process of the invention are valuable starting materials for the manufacture of pesticides, plasticizers, solvents, leather greases, detergents, lubricating oils, synthetic resins and slip agents. They are also assistants in electroplating processes and starting materials for the manufacture of such assistants.

In particular, they act as brighteners for electroplating baths, preferably nickel baths. It has already been disclosed (Ullmanns Encyklopadie der technischen Chemie, volume 7, page 832) to add benzenesulfonates, naphthalenesulfonates, saccharin or p-toluenesulfonylamide to aqueous acid nickel baths to reduce the grain size and increase the gloss, levelling, brightness and elasticity of the nickel deposited on the electroplated articles. Other unsaturated compounds, e.g. allyl alcohol, butynediol, allylurea, acrylic acid and unsaturated amines, and arylsulfimides and arylsulfonic acids have also already been disclosed as brighteners; it is true that they give a finer-grained nickel coating, but they cannot prevent embrittlement and darkening, particularly in areas of low current densities. On the other hand, saturated aliphatic carboxylic acids have been disclosed to be ineffective when used as brighteners. In contrast to these conventional compounds, the end products I, when added to nickel electroplating baths, produce a substantial improvement in respect of gloss, brightness and color of the metal coating which is deposited, hardness, ductility, sensitivity to foreign metal impurities, and improvement in respect of range of applicability, levelling, prevention of pore formation and reduction of spotting and streaking, pitting and brittleness of the nickel surfaces. it is preferred to use from 0.05 to 2 percent by weight, especially from 0.1 to 1 percent by weight, of the new compounds, based on the total weight of liquid in the electroplating bath. Further advantages of using the end products I in electroplating baths are a reduction in pitting on the underside of the articles to be treated, the suppression of hydrogen evolution, which is responsible for such pitting, the achievement of more effective nickel plating at both low and very high current densities and when using extremely high nickel chloride concentrations, and the achievement of a more uniform nickel deposition on articles having an irregular surface, which results in differing current densities. Using the end products I, it is also possible, without difficulty, to work with higher concentrations, in the bath, of other inorganic and organic compounds which are deposited preferentially to nickel and normally lead to blotchiness and reduced gloss.

It is preferred to use the free sulfonic acids IV and their nickel, cobalt, sodium, potassium or magnesium salts. The end products I can be employed alone or together with other nickel brighteners such as acetylene compounds, e.g. butynediol, or pyridinium compounds, e.g. quinaldinium bromide, in the nickel-plating baths. If the new compounds are used conjointly with conventional brighteners such as the arylsulfamides, arylsulfimides or arylsulfonic acids, a synergistic effect is observed in respect of an improvement in brightening, while the disadvantages observed when using the above compounds alone, e.g. spotting, pitting and brittleness of the nickel surfaces, are avoided. If oily impurities are present, it may prove advantageous to use the new compounds together with wetting agents, such as sodium alkyl-sulfates, e.g. sodium lauryl-sulfate, the sodium salt of the sulfuric acid half-ester of lauryl alcohol glycol ether, or sodium salts of sulfosuccinic acid esters, e.g. of the dihexyl ester, in that pitting due to grease and/or foam is prevented.

The end products I of the invention may advantageously be used as additives in the corrosion protection of steel, brass, zinc, copper, aluminum alloys and magnesium alloys, and for the production of bright, hard, very ductile, well-leveled nickel coatings, for example for printing plates, cutting and embossing tools, nickel belts, nickel tubes, screen plates, automobile fenders, watch dials or optical articles. The nickel baths used are as a rule acid electrolytes, e.g. bright nickel baths and semi-mat nickel baths, such as a Watts bath, nickel chloride bath, nickel fluoborate bath or sulfamate bath. Watts baths containing from 250 to 500 grams of nickel sulfate per liter, from 30 to 75 grams of nickel chloride per liter and from 20 to 60 grams of boric acid per liter are preferred. As a rule, the conventional electroplating conditions for nickel electrolytes are adhered to, i.e. preferably temperatures of from 45° to 65° C, current densities of from 3 to 100, preferably from 4 to 10, A/dm$^2$, a rate of travel, of the articles being coated, of from 4 to 6 m/minute, and a pH of from 2.5 to 5.8, preferably from 3.5 to 4.5. Suitable anodes are cast anodes, rolled nickel anodes, electrolytic nickel anodes and nickel anodes in the shape of pelletized moldings, advantageously in a bag. For details of the preparation of the baths, the method of carrying out the electrolytic deposition of the metal, the technique of electroplating and the pretreatment and aftertreatment of the articles to be plated, reference may be made to Ullmanns Encyklopadie der technischen Chemie, volume 7, pages 791–848, and supplementary volume, pages 433 to 436, and to Dettner, Handbuch der Galvanotechnik (Hanser, Munich 1966), especially volume II, pages 87–141.

In the Examples which follow, parts are by weight and bear the same relation to parts by volume as that of the kilogram to the liter.

EXAMPLE 1

2,240 parts of a reaction mixture from the manufacture of dichloropropanesulfochloride (1,300 parts of 1,2-dichloropropane, 380 parts of more highly chlorinated propanes and 560 parts of dichloropropanesulfochloride) are introduced, in the course of 2 hours, into a suspension of 683 parts of sodium bicarbonate in 1,000 parts of water in a cooled stirred vessel at from 10° to 15° C. The temperature is then allowed to rise gradually to 65° C, the pH is brought to 9.5 with 8 parts of sodium carbonate and the mixture is heated for a further 2 hours at 65° C, whilst stirring. The lower layer, which contains the sulfonate-free organic phase and essentially consists of the by-products of the starting mixture, is then separated, at 50° C, from the 2-phase mixture. The 41 percent strength by weight aqueous phase which remains in the stirred vessel and which contains sodium 1-chloro-prop-2,3-ene-3-sulfonate in addition to the sodium chloride formed, is then sprayed in a spray drier at from 200° to 250° C (initial temperature from 90° to 105° C) to give 750 parts of a white powder. After recrystallization from ethanol, 450 parts (95.5% of theory) of sodium 1-chloro-prop-2,3-ene-3-sulfonate of melting point above 300° C (with decomposition) are obtained.

EXAMPLE 2

68.5 parts of sodium 1-chloro-prop-2,3-ene-3-sulfonate manufactured by the method described in Example 1 are dissolved in 103 parts of water and 38.5 parts of hydrochloric acid (36.5 percent strength by weight) are added to the solution in the course of 1 hour, at 25° C. The reaction mixture is then dehydrated under reduced pressure in a rotary evaporator at 50° C and the end product is separated, by dissolving in 100 parts of ethanol, from the sodium chloride which has precipitated. After evaporating off the ethanol, 62.7 parts of 1-chloro-prop-2,3-ene-3-sulfonic acid having an acid number of 344 (95.8% of theory), a chlorine content of 21.75% and a hydrogenation iodine number (determined by the method described in Ullmanns Encyklopadie der technischen Chemie, volume 7, page 546) of 305.

EXAMPLE 3

386 parts of 1,2-dichloropropanesulfochloride are introduced, in the course of 4 hours, into a suspension of 203 parts of calcium hydroxide in 610 parts of water at from 10° to 15° C, in a stirred vessel, whilst cooling. The mixture is then heated at 50° C for 2 hours and at 65° C for a further hour. It is then cooled to room temperature and dried. The calcium salt, mixed with calcium chloride, is obtained as a white powder. On redissolving in i-butanol and reprecipitating, and then recrystallizing from dimethylformamide, 307.5 parts (96% of theory) of calcium 1-chloro-prop-2,3-ene-3-sulfonate having a melting point of > 320° C (with decomposition) and a hydrogenation iodine number of 291 are obtained.

EXAMPLE 4

The reaction is carried out as described in Example 2, with 300 parts of the calcium 1-chloro-prop-2,3-ene-3-sulfonate obtained from Example 3. 250 parts (93.3% of theory) of liquid 1-chloro-prop-2,3-ene-3-sulfonic acid, having an acid number of 359 and a hydrogenation iodine number of 311, are obtained.

EXAMPLE 5

The reaction is carried out as described in Example 1, with 20 parts of 1,1,2-trichloropropanesulfonic acid chloride. 16.3 parts (94% of theory) of sodium 1,1-dichloro-prop-2,3-ene-3-sulfonate, having a chlorine content of 33.2% and a hydrogenation iodine number of 355, are obtained.

EXAMPLE 6

The reaction is carried out as described in Example 2, with 15 parts of sodium 1,1-dichloro-prop-2,3-ene-3-sulfonate obtained from Example 5. 12.5 parts (93% of theory) of 1,1-dichloro-prop-2,3-ene-3-sulfonic acid having an acid number of 298, a chlorine content of 36.6% and a hydrogenation iodine number of 395 are obtained.

EXAMPLES 7 to 9 (USE)

Polished copper sheets and brass sheets are electroplated at 60° C with and without agitation of the bath. The composition of the Watts electrolyte used is:

Nickel sulfate: 300 g/l
Nickel chloride: 50 g/l
Boric acid: 35 g/l
Sodium salt of hexyl sulfosuccinate: 0.5 g/l The pH in the Watts bath is from about 3.5 to 4.5; an electrolytic nickel anode in a bag, a current density of from 0.5 to 12 A/dm$^2$ (Hull cell) and en electrolysis time of 10 minutes are used.

In the Examples which follow, the additives shown in the Table are in each case added, in various combinations, to a base electrolyte.

| Example | Additive | Amount g/l | Notes |
|---|---|---|---|
| 7 | Sodium salt of 1-chloro-propenylsulfonic acid | 2 | very bright nickel coatings over a current density range from <0.5 A/dm$^2$ to >12 A/dm$^2$; subsequent chroming is easy |
|  | Benzenesulfonamide | 3 |  |
|  | 1,4-Di-(2-hydroxy-ethoxy)-butyne-2 | 0.25 |  |
| 8 | Sodium salt of 1-chloro-propenylsulfonic acid | 2 | bright over the current density range from <0.5 to >12 A/dm$^2$ |
| 9 (Comparison) | Sodium salt of allyl-sulfonic acid | 2 | hazy over the enture current density range |
| 10 (Comparison) | Sodium salt of allyl-sulfonic acid | 10 | bright over the current density range from <0.5 to >12 A/dm$^2$, but less gloss and lower ductility; very passive toward subsequent chroming |
| 11 (Comparison) | Saccharin | 2.5 | bright over the current density range from 1.5 A/dm$^2$ to 11 A/dm$^2$ (slight haze in the lower current density range); very low ductility and difficulty in chroming |
|  | But-2-yne-1,4-diol | 0.25 |  |
|  | Propargyl alcohol | 0.05 |  |
| 12 | Sodium salt of 1-chloro-propenylsulfonic acid | 1 | very bright over the current density range from <0.5 to >12 A/dm$^2$ |
|  | Saccharin | 1.5 |  |
|  | But-2-yne-1,4-diol | 0.25 |  |
|  | Propargyl alcohol | 0.15 |  |
| 13 (Comparison) | Saccharin | 2.5 | dark blotches over the entire current density range |
|  | But-2-yne-1,4-diol | 0.25 |  |
|  | Propargyl alcohol | 0.05 |  |
|  | Copper sulfate (100 ppm) |  |  |
| 14 | Sodium salt of 1-chloro-propenylsulfonic acid | 1 | very bright over the current density range from <0.5 A/dm$^2$ to >12 A/dm$^2$ (no dark blotches) |
|  | Saccharin | 1.5 |  |
|  | But-2-yne-1,4-diol | 0.25 |  |
|  | Propargyl alcohol | 0.05 |  |
|  | Copper sulfate (100 ppm) |  |  |
| 15 | Nickel salt of 1-chloro-propenylsulfonic acid | 2 | very bright over the current density range from <0.5 to >12 A/dm$^2$ |
| 16 | 1,1-Dichloropropenyl-3-sulfonic acid | 2 | bright over the current density range from <0.5 to >12 A/dm$^2$ |
| 17 | Sodium 1,1-dichloropropenyl-3- | 2 | bright over the current density range from <0.5 to >12 A/dm$^2$ |
| 18 | Nickel 1,1-dichloropropenyl-3-sulfonate | 2 | bright over the current density range from <0.5 to >12 A/dm$^2$ |
| 19 | Calcium 1-chloropropenyl-3-sulfonate | 2 | bright over the current density range from <0.5 to >12 A/dm$^2$ |

Compared to the nickel coatings obtained with the comparative electrolyte the nickel coatings obtained from baths containing the additives of the invention are brighter, more elastic and of a more pleasant shade, and exhibit lower grain size, comparatively less, or no, pitting, no blotches, tarnishing or haziness on the surfaces of the article, and better levelling, and therefore a thinner coating, coupled with uniform deposition over the entire surface of the article, and therefore require less subsequent grinding and polishing, and achieve a saving of nickel.

We claim:

1. 1-Chloro-prop-2-ene-3-sulfonic acid compounds of the formula

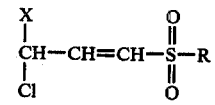

where X is hydrogen or chlorine, R is hydroxyl or —OY and Y is one equivalent of nickel, cobalt, cadmium, zinc, mercury, sodium, potassium, calcium or magnesium.

2. A compound as set forth in claim 1, wherein R is hydroxyl.

3. A compound as set forth in claim 1, wherein R is OY and wherein Y is one equivalent of nickel, cobalt, sodium, potassium or magnesium.

4. A compound as set forth in claim 3, wherein Y is sodium.

* * * * *